(12) United States Patent
Seippel (10) Patent No.: US 10,260,034 B2
(45) Date of Patent: *Apr. 16, 2019

(54) CULTURE FLASK

(71) Applicant: Eppendorf AG, Hamburg (DE)

(72) Inventor: Martin Seippel, Ammersbek (DE)

(73) Assignee: Eppendorf AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,575

(22) Filed: Mar. 23, 2017

(65) Prior Publication Data

US 2017/0191012 A1   Jul. 6, 2017

Related U.S. Application Data

(63) Continuation of application No. 14/083,048, filed on Nov. 18, 2013, now Pat. No. 9,708,576.

(Continued)

(30) Foreign Application Priority Data

Jan. 18, 2013   (EP) ..................................... 13000264

(51) Int. Cl.
  *C12M 1/24*   (2006.01)
  *C12M 1/26*   (2006.01)
  *C12M 1/00*   (2006.01)

(52) U.S. Cl.
  CPC ............ *C12M 33/04* (2013.01); *C12M 23/02* (2013.01); *C12M 23/08* (2013.01)

(58) Field of Classification Search
  CPC ....... C12M 23/02; C12M 23/08; C12M 33/04
  See application file for complete search history.

(56) References Cited

U.S. PATENT DOCUMENTS

| 4,334,028 A | 6/1982 | Carver |
| 5,112,957 A | 5/1992 | Pollard |

(Continued)

FOREIGN PATENT DOCUMENTS

| CN | 202415564 | 9/2012 |
| EP | 141104 | 5/1985 |

(Continued)

OTHER PUBLICATIONS

The best conditions for your cells: Eppendorf Tissue Culture Consumables Eppendorf Tissue Culture Consumables, 2012, Eppendorf India Limited, www.eppendorf.com/worldwide, Kilpuk, Chennai.

*Primary Examiner* — Jonathan M Hurst
(74) *Attorney, Agent, or Firm* — Vidas, Arrett & Steinkraus, P.A.

(57) ABSTRACT

A culture flask comprising a culture chamber in a flask body comprising an even bottom wall with a growth surface on the top side, an even cover wall at a section from the bottom wall, and side walls that bridge the distance between the margins of the bottom wall and cover wall, an opening that is in adjacent regions of a side wall and the even cover wall at a distance from the bottom wall, and a hollow cylindrical flask neck that is connected to the margin of the opening and is aligned at a sharp angle to the growth surface so that the serological pipette, a scraper, a cannula or another elongated device for adding or removing material can be placed on the rear corners of the growth surface from the outside through the flask neck.

2 Claims, 6 Drawing Sheets

Related U.S. Application Data

(60) Provisional application No. 61/754,180, filed on Jan. 18, 2013.

(56) References Cited

U.S. PATENT DOCUMENTS

| | | |
|---|---|---|
| 5,139,952 A | 8/1992 | Honda et al. |
| 5,783,440 A | 7/1998 | Stevens |
| 2006/0205065 A1* | 9/2006 | Bossi .................. C12M 23/08 435/304.3 |

FOREIGN PATENT DOCUMENTS

| | | |
|---|---|---|
| EP | 743362 | 4/2002 |
| JP | 2004-141072 | 5/2004 |
| WO | 2006099127 | 9/2006 |

* cited by examiner

CULTURE FLASK

CROSS-REFERENCE TO RELATED APPLICATIONS

This application claims priority to U.S. 61/754,180, filed on Jan. 18, 2013 and U.S. Ser. No. 14/083,048 filed Nov. 18, 2013, the disclosures of which are incorporated herein by reference and to EP 13000264.5 filed on Jan. 18, 2013, priority of which is claimed.

STATEMENT REGARDING FEDERALLY SPONSORED RESEARCH

Not applicable.

BACKGROUND OF THE INVENTION

The invention relates to a culture flask for cultivating cells, tissues or microorganisms.

Culture flasks (also termed "cell culture flasks") are used in the laboratory to grow and obtain cells, tissues or microorganisms. They have a flat, substantially rectangular flask body with a bottom wall, cover wall and side walls that delimit a culture chamber. The top side of the bottom wall is a growth surface for cells, tissue or microorganisms. A flask neck with a lid projects to the outside from a narrow, front side wall. When used, the large bottom wall of culture flasks is normally placed on a horizontal base. The distance between the even bottom wall and the even cover wall of the culture flask is termed the height or thickness. When stacked, culture flasks can be arranged in a space-saving manner in an incubator that provides the climate for growing the cells, tissue or microorganisms. The lid can frequently be moved from a closed to a ventilation position, or is designed as a filter lid to ensure an exchange of gas between the incubator and culture chamber in the flask body.

Cells, tissue or microorganisms can be removed from the culture flask by means of a serological pipette, scraper or cannula that is inserted from the outside through the flask neck into the culture chamber toward the growth surface. Nutrient medium is also pipetted into or out of the culture flask through the flask neck by means of the serological pipette. These tasks are difficult, especially when they are performed at a sterile bench while the user is wearing protective clothing.

At a distance from the bottom wall, the bottle neck is connected to the margin of an opening in the side wall to prevent fluid from sloshing out of the culture chamber when the culture flask is opened. The opening is therefore delimited at the bottom by the distance between the bottle neck and the bottom wall, and at the top by the straight-line joint edge along which the top margin of the side wall is connected to the cover wall. To make it easier to access the growth surface with a serological pipette or a scraper, culture flasks are known that have a flask neck that is inclined toward the growth surface at a sharp angle. It is difficult for the serological pipette or the scraper to reach, in particular, the rear corners of the growth surface due to the edge of the top margin of the opening. Gliding the serological pipette or scraper along this edge is in fact associated with greater resistance than gliding along the smooth surface of the cylindrical flask neck.

EP 0 743 362 B1, the entire contents of which is incorporated herein by reference, describes a laboratory flask comprising a flask body that has a circular opening in a front side wall. An elongated annular flask neck with an inner and outer cylindrical wall extends outward from the margin of the opening. Part of the inside of the flask neck is arranged above the cover wall of the flask body. The flask neck has a pendant filling wall which closes the gap between the inside of the flask neck and the cover wall close to the front side wall. With this laboratory flask, access to the growth surface is limited by the filling wall at the top margin of the opening.

WO 2006/099127 A1, the entire contents of which are incorporated herein by reference, describes a cell culture flask comprising a flask body that serves as a cell culture chamber. The cell culture chamber is delimited by a bottom tray with a rigid surface and by a cover wall, the bottom tray and cover wall being connected to each other at side and end walls. In at least one opening, there is an angled flask neck, and at least one screw-on lid is aligned with the opening of the flask neck. In addition to the angled flask neck, the bottom wall and cover wall have recesses that rise and fall toward the flask neck so that no liquid remains captured in the corners. The angled flask neck improves the access to the cell culture chamber by a pipette, scraper or cannula. In addition, the rising and falling recesses provide free space for the lid so that it does not collide with a neighboring cell culture flask in a stack. The flask neck is preferably arranged at a corner of the cell culture flask so that the cell culture surface can be larger.

Against this background, an object of the invention is to provide a culture flask that makes it easier for a serological pipette, scraper, cannula or other elongated device to access the growth surface on the bottom wall for adding or removing material.

BRIEF SUMMARY OF THE INVENTION

The culture flask has:
a culture chamber in a flask body comprising an even bottom wall with a growth surface on the top side, an even cover wall at a distance from the bottom wall, and side walls that bridge the distance between the margins of the bottom wall and cover wall,
an opening that is in adjacent regions of a side wall and the even cover wall at a distance from the bottom wall, and
a hollow cylindrical flask neck that is connected to the margin of the opening and is aligned at a sharp angle to the growth surface so that the serological pipette, a scraper, a cannula or another elongated device for adding or removing material can be placed in particular on the rear corners of the growth surface from the outside through the flask neck.

With the culture flask according to the invention, the opening in the flask body is formed in two adjacent regions of a side wall and the cover wall. The opening therefore has two opening sections, wherein a bottom opening section is arranged in a side wall, and a top opening section is arranged in the cover wall. The hollow cylindrical flask neck angled at a sharp angle to the growth surface is connected to the margin of the opening, i.e., to the margin of the bottom opening section and the margin of the top opening section. Since the hollow cylindrical flask neck is connected to the margin of the opening, its inner cross section is not partially covered by the margin of the opening. A serological pipette, scraper or a different elongated device for adding or removing material can be inserted through the flask neck and the opening in the side wall and cover wall into the culture chamber in the flask body and can be placed on the growth surface and adjacent inner surfaces of the rear and lateral side walls. This is simpler than with conventional culture flasks, in particular because the opening does not cover the inner cross section of the flask neck at the top by a straight-line joint edge. Consequently, access to the growth surface is easier, in particular at the rear corners of the growth surface opposite the flask neck. The culture flask can be designed such that the inner surfaces of the rear side wall opposite the flask neck, and the two longitudinal side walls neighboring thereto, are easier to reach with a serological pipette, a scraper, a cannula or another elongated device, thus making it easier to aim the elongated device toward the two rear corners of the cell culture flask.

The flask neck is a hollow cylinder, at least at the opening, to make it easier for the growth surface to be accessed by an elongated device for adding and removing material. At a distance from the opening, the flask neck can also have a shape that deviates from a hollow cylinder. The flask neck is preferably entirely a hollow cylinder.

According to another embodiment, the flask neck has a plurality of hollow cylindrical flask neck parts. According to another embodiment, the hollow cylindrical flask neck parts are arranged sequentially in the longitudinal direction of the flask neck. According to another embodiment, the hollow cylindrical flask neck parts have different inner diameters and/or different outer diameters. According to another embodiment, a hollow cylindrical flask neck part with a larger inner diameter is arranged further to the rear than a hollow cylindrical flask neck part with a smaller inner diameter. Consequently, the flask neck expands from front to rear. This is advantageous, especially for reaching the rear corners by means of an elongated device for adding or removing material. According to another embodiment, a flask neck composed of a plurality of components has flask neck parts that possess different inner diameters and/or different outer diameters.

According to one embodiment, the cell culture flask has a flask base and a flask bonnet, wherein the flask base comprises the bottom wall, the side walls, and a first flask neck part connected to a side wall, the flask bonnet comprises the cover wall and a second flask neck part connected to the cover wall, and the flask base and flask bonnet are connected to each other in a sealing manner at neighboring margins. The flask base and flask bonnet are advantageously producible from plastic by means of injection molding and another suitable method. The flask base and flask bonnet are preferably each produced as a single part by injection molding. The flask base and flask bonnet are preferably unreleasably connected to each other in a sealing manner at neighboring margins. Alternatively, the flask base and flask bonnet are releasably connected to each other at the neighboring margins, for example by means of a snap connection, wherein a soft elastic sealing element can be arranged between the neighboring margins for a seal.

According to another embodiment, the first flask neck part is a hollow cylinder which, in a bottom margin section of an end face margin that runs in a surface perpendicular to the growth surface, is connected to the margin of a bottom opening section of the opening in the side wall, and the second flask neck part is a hollow cylinder segment that is connected at an end face margin to a top margin section of the end face margin of the first flask neck part, and is connected at its longitudinal margin to the margin of a top opening section in the cover wall that expands toward the first flask neck part. This embodiment is in particular advantageous for producing the flask base and flask bonnet by injection molding.

According to another embodiment, the hollow cylinder segment has a larger inner diameter than the hollow cylinder.

According to another embodiment, the front margin of the hollow cylinder segment is connected at the inner perimeter to the outer perimeter of the rear margin of the hollow cylinder.

Furthermore, this embodiment is advantageous for connecting the flask base and flask bonnet.

According to another embodiment, the connection between the flask base and flask bonnet is an ultrasonic welded connection, or an infrared welded connection, or an adhesive connection, or a snap connection.

In ultrasonic welding, the materials are melted together by high frequency vibrations of the joining partners (the flask base and flask bonnet) and are thereby joined to each other. The vibration is generated by an ultrasonic generator and introduced into a joining partner by means of a tool (a so-called sonotrode). The integral connection between the flask base and flask bonnet is very strong. Ultrasonic welding can be advantageously used in particular when the flask base and flask bonnet are made of polystyrene.

In the case of infrared welding, the joining partners are melted by radiating heat into the joint zones. For example, an infrared radiator is placed next to the joining zones between the flask base and flask bonnet. After the joint zones are melted, the joining partners are joined. This is done for example after the infrared radiator is removed by pressing the flask base and flask bonnet together.

In the case of adhesion, an adhesive is introduced between the joining partners. In addition, it should be ensured that the adhesive or solvent contained therein is harmless to the cells, tissue or microorganisms to be cultivated. In addition or alternately, the adhesive connection is encapsulated from the culture chamber, for example by separating the adhesive connection from the culture chamber with a seal.

According to another embodiment, the ultrasonic welded connection between the flask base and flask bonnet is created by welding an energy director that projects downward and runs around the margin of the flask bonnet into a groove that is open at the top and runs around the top margin of the flask base. The energy director is preferably welded into the groove by means of a sonotrode placed on the top side of the flask bonnet. The energy introduced by the sonotrode into the flask bonnet by means of the energy director is introduced into the base of the groove. The molten material collects in the groove and fills it up. After the molten material hardens, the flask base and flask bonnet are permanently connected to each other in a sealing manner. The contours of the groove and energy director then no longer exist, or only partially exist, or are replaced by the integral connection between the flask bonnet and flask base.

According to a preferred embodiment, the energy director before welding has the shape of a rib with a triangular cross-section and a tip of the triangle at the bottom end. It is also preferable for the angle between the side surfaces of the energy director at the tip to be 50° to 70°, and even more preferably to be approximately 60°. Before welding, it is preferable for there to be a small lateral gap between the energy director and the side walls of the groove.

According to another embodiment, the margin of the flask bonnet has an upwardly projecting, uninterrupted or interrupted peripheral first rib. The first rib is advantageously useful for mounting a sonotrode. For this purpose, the first rib is preferably arranged in a vertical direction above the energy director. The energy can be introduced by the sonotrode via the first rib through the cover wall directly into the energy director. In addition, placing the sonotrode on the first rib prevents damage to the cover wall that can result when the sonotrode is placed flat on the cover wall. Furthermore, the first rib can serve as a guide element that prevents an additional culture flask placed on the culture flask from shifting to the side.

According to another embodiment, an uninterrupted or interrupted peripheral second rib with an even bottom side projects downward from the bottom wall. The bottom side of the second rib forms a contact area. Furthermore, the second rib can serve as a guide element that prevents the culture flask from shifting laterally when it is placed on a culture flask. For this, the second rib is preferably arranged laterally offset from the first rib.

According to another embodiment, the infrared welded connection between the flask base and flask bonnet is created by melting and pressing together a downward-projecting third rib running around the margin of the flask bonnet, and an upward-projecting fourth rib running around the top margin of the flask base. The third and fourth ribs preferably have a rectangular cross section and are welded together at strip-shaped end faces. This geometry promotes the intended heating and welding of the joint zones together.

According to another embodiment, the flask neck has at least one outer thread and/or at least one snap element for a lid. By means of the outer thread and/or the snap element, a lid provided with complementary elements can be releasably affixed—and/or adjustably affixed from a closed position to a ventilation position—to the cell culture flask.

According to another embodiment, the cell culture flask narrows toward the flask neck. This makes it easier to pour medium out of the cell culture flask. In addition, narrowing the cell culture flask eliminates regions of a growth surface that are unreachable by means of a serological pipette or a different supply and removal device.

According to another embodiment, a sloping wall angled at a sharp angle to the bottom wall is between the bottom wall and side wall to which the flask neck is attached. The sloping wall makes it easier to pour medium out of the culture flask and to move the elongated device for supplying or removing material.

According to a further embodiment, the flask neck is cylindrical. According to a preferred embodiment, the flask neck is a regular cylinder. The cylindrical and regular cylindrical shape makes it easier to move a serological pipette, or another elongated device, within the flask neck with little resistance.

According to another embodiment, the transition between the flask neck and the inside of the culture chamber is completely or partially smooth and/or rounded. This makes it easier to move the serological pipette, or a scraper or a different elongated device for supplying or removing material, within the flask neck.

According to another embodiment, the even cover wall is aligned parallel to the even bottom wall.

According to another embodiment, the bonnet and base of the culture flask are coordinated with each other such that a plurality of equivalent cell culture flasks can be stacked on each other.

According to another embodiment, the side wall to which the flask neck is attached has, below the flask neck, an arced cut-out that is suitable for accommodating the region of the flask neck projecting from the cover wall of an equivalent culture flask disposed underneath. This makes it possible to stack culture flasks on each other.

According to a further embodiment, the culture flask is produced by injection-molding. The culture flask preferably consists of a flask base and a flask bonnet that are produced separately by injection molding and then connected to each other in a sealing manner.

According to a further embodiment, the culture flask is made of polystyrene or another plastic.

BRIEF DESCRIPTION OF THE SEVERAL VIEWS OF THE DRAWINGS

The invention is explained in greater detail below based on included drawings of an exemplary embodiment. The drawings show.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated In the present application, the designations "top", "above", "bottom" and "below" refer to the alignment of a culture flask of the bottom wall on a horizontal base and of the cover wall above the bottom wall. The designations "front" and "rear" refer to a culture flask where the flask neck is closer to the viewer than the flask body.

According to FIGS. 1 to 5, a culture flask 1 according to the invention comprises a flask body 2 with a substantially even bottom wall 3 and a substantially even cover wall 4 that are aligned parallel to each other. The bottom wall 3 and the cover wall 4 each have a substantially rectangular section 3.1, 4.1 and a substantially trapezoidal section 3.2, 4.2.

The distance between the bottom wall 3 and the cover wall 4 is bridged by side walls 5, 6, 7, 8, 9, 10 that are connected to the margins of the bottom wall 3 and the cover wall 4. The rectangular section of the bottom wall 3.1 is slightly smaller than the rectangular section 4.1 of the cover wall 4. Consequently, the rear side wall 5 and the two rear longitudinal side walls 6, 7 that are connected to the margins of the rectangular sections 3.1, 4.1 only angle outward slightly (see FIG. 12a).

The trapezoidal section 3.2 of the bottom wall 3 is significantly smaller than the trapezoidal section 4.2 of the cover wall 4. Consequently, the front longitudinal side walls 8, 9 that connect the two side margins of the trapezoidal sections 3.2, 4.2 to each other angle outward more strongly (see FIG. 12a).

The front margin of the trapezoidal section of the bottom wall is connected to a trapezoidal sloping wall 11. The front margin of the sloping wall 11 terminates slightly to the rear of the front margin of the cover wall 4 (see FIG. 12a). The front side wall 10 is arranged between this margin of the sloping wall 11 and the front margin of the cover wall 4. The front side wall 10 extends below the front margin of the sloping wall 11 to the level of the bottom side of the bottom wall 3 (see FIG. 1, 3).

Figure 7:
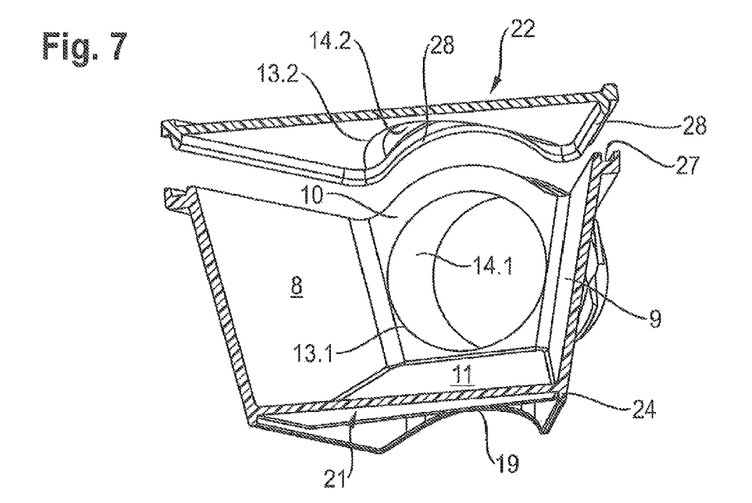
FIG. 7 A vertical partial section of a flask base and flask bonnet before being joined from a perspective at an angle from below and from the side.
Figure 8:
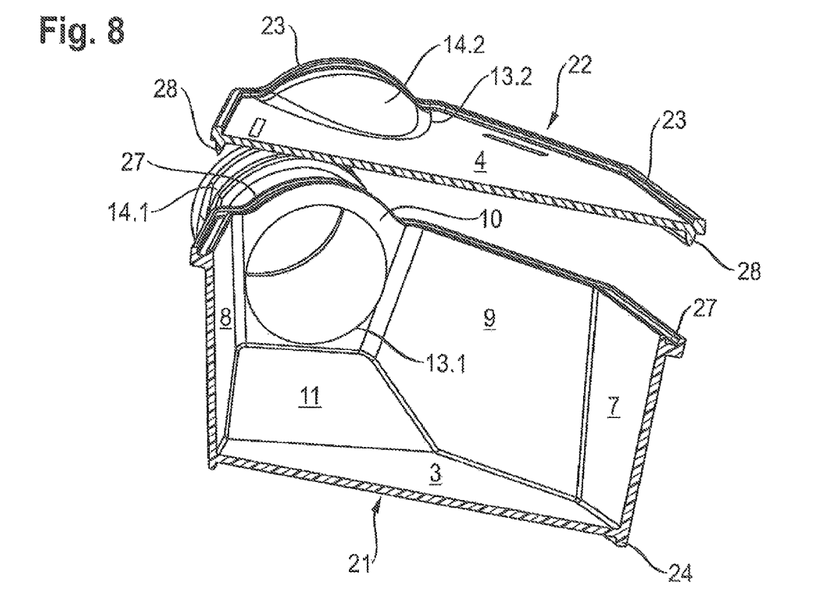
FIG. 8 A vertical section of a flask base and flask bonnet before being joined from a perspective at an angle from above and from a different side.

The front longitudinal side walls 8, 9 also bridge the distance between the longitudinal margins of the inclined surface 11 and the front longitudinal margins of the cover wall 4 (see FIG. 7, 8).

The top side of the bottom wall is an even growth surface 12.

There is an opening 13 in a region of the front side wall 10 adjacent to the cover wall 4 and in the adjacent region of the cover wall 4. A bottom opening section 13.1 of the opening 13 that is disposed in the front side wall 10 is disposed above the sloping wall 11. The opening 13 is therefore at a distance from the bottom wall 3 in a vertical direction. The bottom opening section 13.1 is elliptical when viewed from the front (see FIG. 10).

A top opening section 13.2 that is disposed in the cover wall 4 expands toward the front side wall 10. In a plan view, the top opening section 13.2 has the shape of a section of an ellipse (see FIG. 4, 7, 8).

A hollow cylindrical flask neck 14 is securely connected to the margin of the opening 13. The flask neck 14 is angled at a sharp angle relative to the bottom wall 3. At the front end, the flask neck 14 extends upward beyond the section of the cover wall 4 that is aligned parallel to the bottom wall 3.

The flask neck 14 has a circular cross section. It has a first flask neck part 14.1 that possesses the shape of a hollow cylinder. At a bottom margin section 15.1 of an end face margin 15, the first flask neck part 14.1 is securely connected to the margin of the bottom opening section 13.1 (see FIG. 3).

Furthermore, the flask neck 14 has a second flask neck part 14.2 that is a hollow cylinder segment. The second flask neck part 14.2 is connected at the lateral margins to the elliptical margin of the top opening section 13.2. At its end face margin, it is connected to its top margin section 15.2 of the first flask neck part 14.1 that projects upward beyond the front side wall 10.

On the outside circumference, the flask neck 14 has a thread 16 for adjusting a lid.

Below the flask neck, the front side wall 10 has an arced cut-out 19 that is shaped to be complementary with the front end face margin of the second flask neck part 14.2.

The walls 3 to 11 delimit a culture chamber 20.

Figure 6:
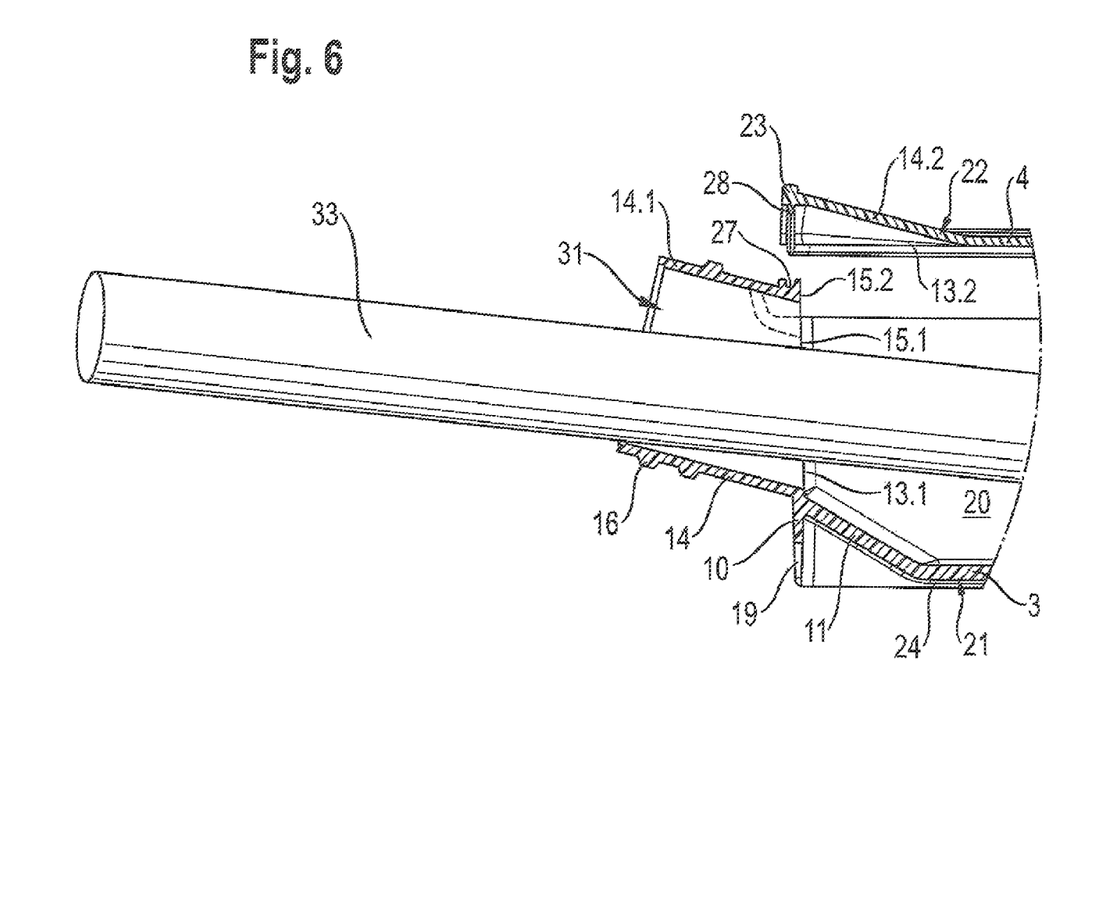
FIG. 6 A partial longitudinal section of a flask base and flask bonnet of the culture flask before being joined.

The bottom wall 3 as well as the side walls 5 to 10 and the first flask neck part 14.1 belong to a flask base bottom part 21 that is shown in FIGS. 6 to 8. The cover wall 4 and the second flask neck part 14.2 belong to a flask bonnet 22 that is shown in the same figures.

At the margin, the flask bonnet 22 has an upwardly projecting, uninterrupted peripheral first rib 23.

A peripheral second rib 24 projects downward from the margin of the bottom wall 3.

Figure 5:
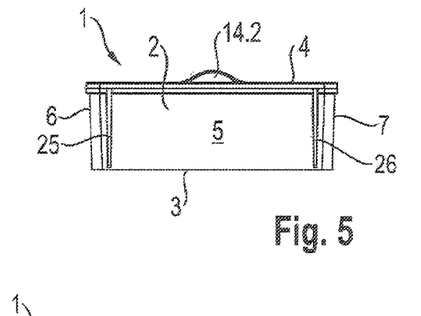
FIG. 5 A rear view of the culture flask.

On the rear side wall 5 next to the lateral margins, there are two vertically extending rear ribs 25, 26 that project to the rear (see FIG. 5).

At the top margin, the flask base 21 has a peripheral groove 27 that is open at the top (see FIGS. 6 to 7). This extends along the top margins of the rear and longitudinal side walls 5, 6, 7, 8, 9 and next to the first flask neck part 14.1 on the top margin of the front side wall 10. Furthermore, it extends at the rear end of the first flask neck part 14.1 beyond on the perimeter of first flask neck part 14.1. Accordingly, the groove 27 only extends in an arc on the perimeter of the first flask neck part 14.1, and the remainder extends in a plane.

The flask bonnet 22 has a peripheral, downwardly projecting energy director 28 at the margin. According to FIGS. 6 to 8, this has the shape of a rib with a triangular cross section, and the tip of the rib points downward. The energy director 28 runs along the rear and side margins of the cover wall 4 and next to the second flask neck part 14.2 along the front margin of the cover wall. Furthermore, it extends at the front along the inner perimeter of the second flask neck part 14.2.

The energy director 28 is arranged vertically below the first rib 23.

Figures 1, 4:
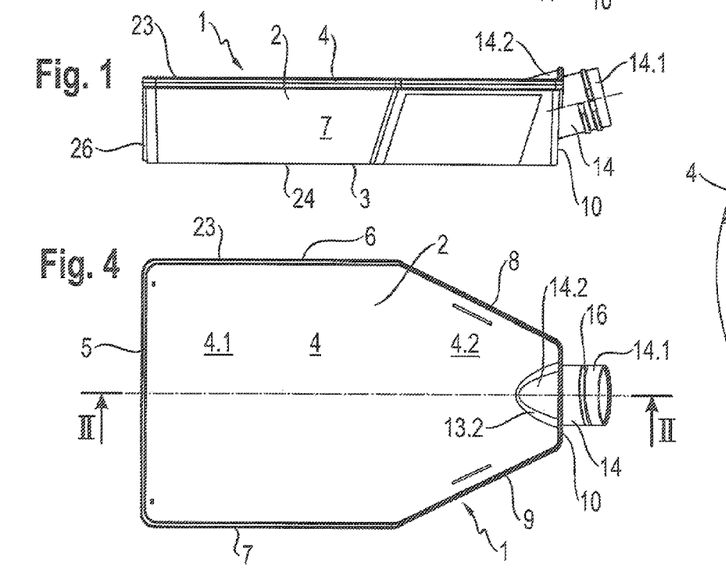
FIG. 1 A side view of the culture flask.
FIG. 4 A plan view of the culture flask.
Figure 2:
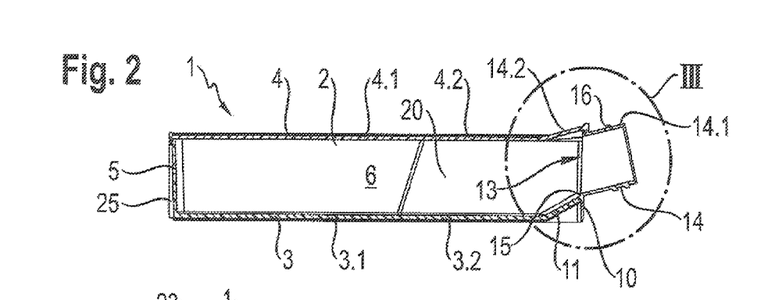
FIG. 2 A longitudinal section of the culture flask.
Figure 3:
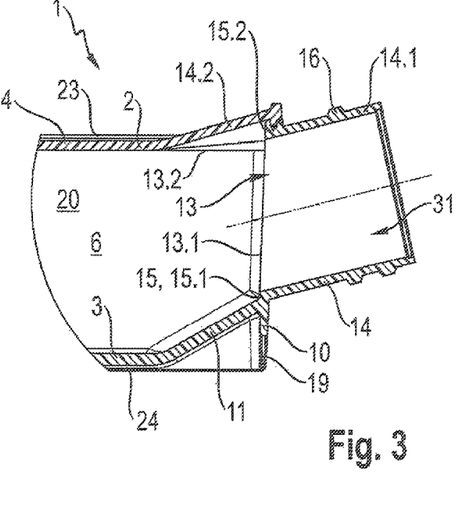
FIG. 3 An enlarged detail view III from FIG. 2 of the culture flask.

During production, the flask bonnet 22 is placed on the flask base 21 such that the energy director 28 engages in the groove 27. This is shown in FIGS. 2 and 3. Then a sonotrode with a corresponding shape is placed from above on the first rib 23. The sonotrode is caused to vibrate in a vertical direction at a frequency in the ultrasonic range. By means of the friction between the energy director 28 and the base of the groove 27, the plastic material is melted and welded together. FIGS. 2 and 3 show the flask bonnet 22 and flask base 21 in the end position after ultrasonic welding, and the tip of the energy director 28 that exists before welding is drawn in FIGS. 2 and 3 to illustrate the part of the energy director melting together with the groove 27 during welding.

Figure 9:
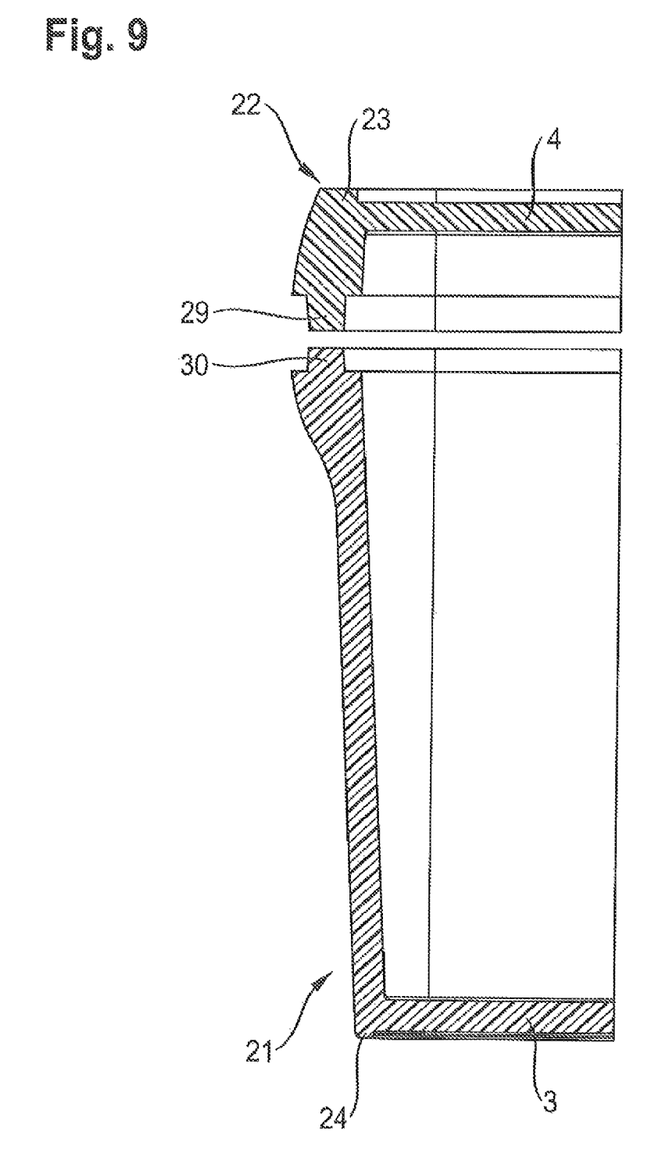
FIG. 9 A vertical section of an alternative embodiment of the joint zones of the flask base and flask bonnet for an infrared welded connection before being joined.

Alternately, the flask base 21 and the flask bonnet 22 according to FIG. 9 have a geometry for producing an infrared welded connection. The geometry comprises a third peripheral rib 29 projecting downward from the flask bonnet 22, and a peripheral fourth rib 30 projecting upward from the flask base. To produce the connection, an infrared radiator is disposed between the third and fourth rib 29, 30 and is removed after the third and fourth rib 29, 30 have melted. Then the melted ribs 29, 30 are pressed together and, after hardening, are firmly connected to each other.

Figure 10:
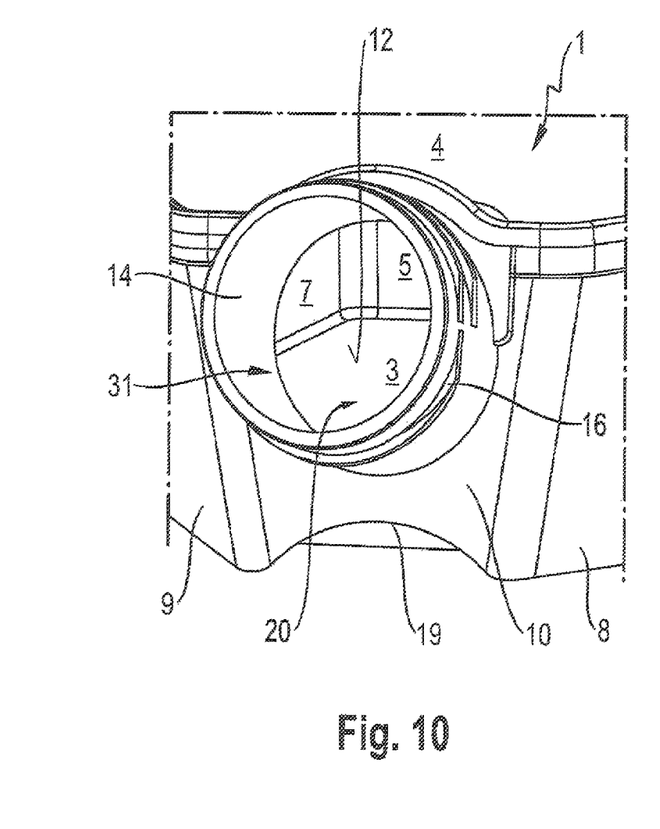
FIG. 10 The culture flask in a perspective view diagonally from the front and from the side.
Figure 11:
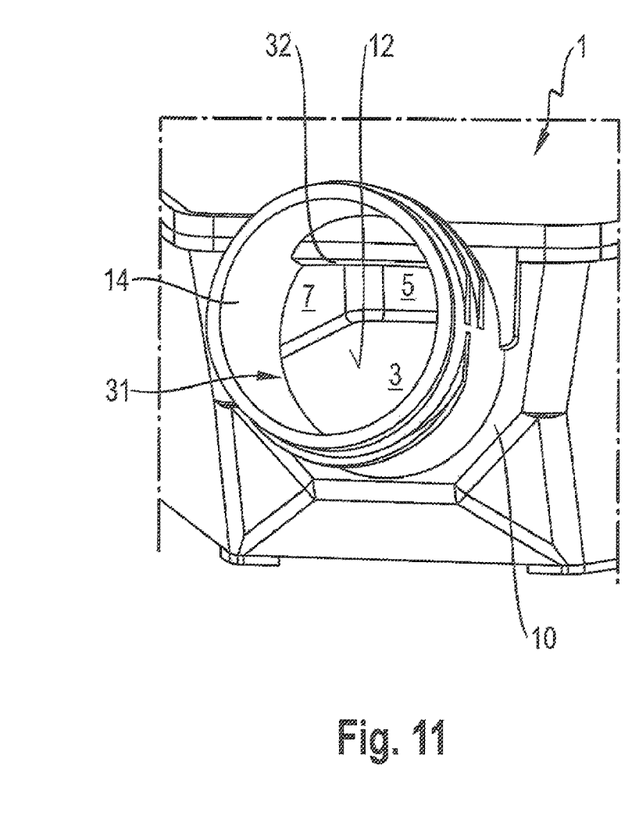
FIG. 11 A conventional culture flask in a perspective view diagonally from the front and from the side.

According to FIG. 10, a passage 31 in the culture flask 1 according to the invention through the flask neck 14 is not delimited by a horizontal edge in the region of the opening 13. The culture chamber 20 is therefore easily accessible. According to FIG. 11, an edge 32 in a conventional culture flask 1 hinders access through the flask neck into the culture chamber 20.

Figures 12A, 12B:
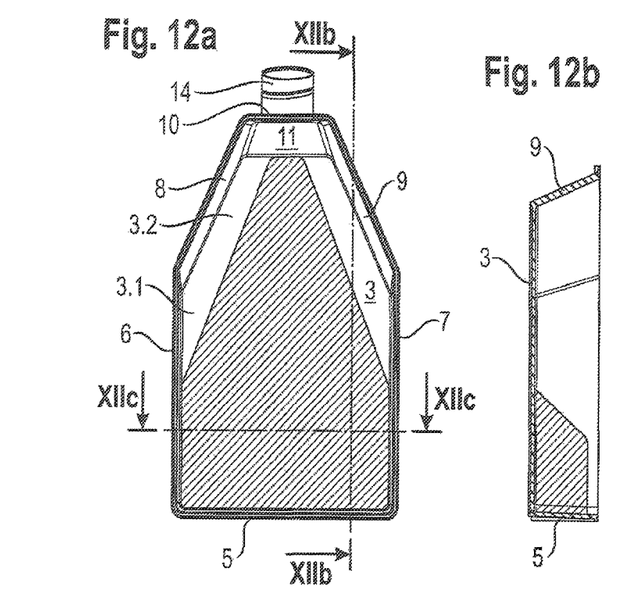
FIG. 12a-c A plan view of the surfaces within the culture flask according to the invention which can be reached by means of a serological pipette (FIG. 12a); in a section along line b-b from FIG. 12a (FIG. 12b) and in a section along line c-c from FIG. 12a (FIG. 12c)
Figure 12C:
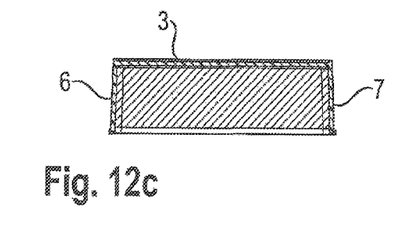
Figure 13A:
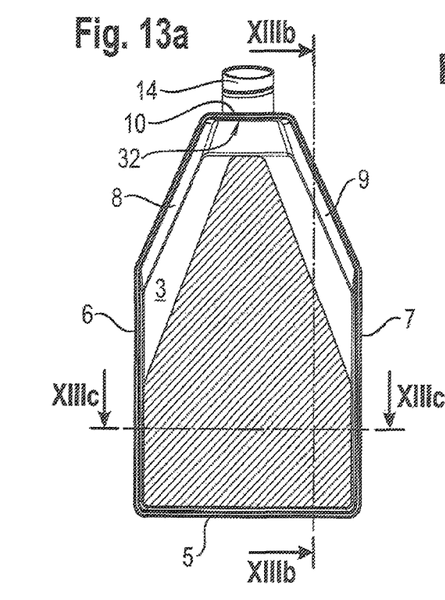
FIG. 13a-c A plan view (FIG. 13a) of the surfaces within the conventional culture flask which can be reached by means of a serological pipette; in a section along line b-b from FIG. 13a (FIG. 13b) and in a section along line c-c from FIG. 13a (FIG. 13c).
Figure 13B:
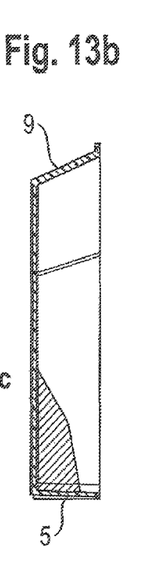
Figure 13C:
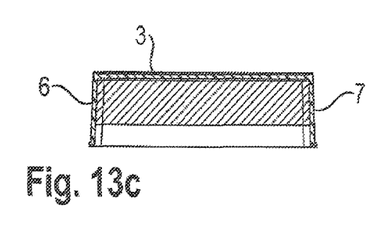

According to FIG. 12, a large part of the growth surface 12 and comparatively large parts of the rear seat wall 5 and longitudinal side walls 6, 7 of the culture flask 1 according to the invention are reachable with a serological pipette 33 (see FIG. 6) with a dose volume of 25 ml that is inserted through the flask neck 14 from the outside. According to FIG. 13, only a corresponding part of the growth surface 12 and a small part of the rear side wall 5 and lateral side walls 6, 7 are reachable with the serological pipette 33 in a conventional culture flask 1. The surfaces of the side walls 5, 6, 7 reachable by the pipette 33 are cross-hatched in FIGS. 12 and 13. With the culture flask 1 according to the invention, it is hence easier to supply and remove cells, tissue, microorganisms and nutrient medium than is the case with a conventional culture flask 1.

This completes the description of the preferred and alternate embodiments of the invention. Those skilled in the art may recognize other equivalents to the specific embodiment described herein which equivalents are intended to be encompassed by the claims attached hereto.

LIST OF REFERENCE NUMBERS

1 Culture flask
2 Flask body
3 Bottom wall
3.1 Rectangular section
3.2 Trapezoidal section
4 Cover wall
4.1 Rectangular section
4.2 Trapezoidal section
5-10 Side walls
11 Sloping wall
12 Growth surface
13 Opening
13.1 Bottom opening section
13.2 Top opening section
14 Flask neck
14.1 First flask neck part
14.2 Second flask neck part
15 End face margin
15.1 Bottom margin section
15.2 Top margin section
16 Thread
19 Cut-out
20 Culture chamber
21 Flask bottom part
22 Flask top part
23 First rib
24 Second rib
25, 26 Rear rib
27 Groove
28 Energy director
29 Third rib
30 Fourth rib
31 Passage
32 Edge
33 Pipette

What is claimed is:

1. A culture flask comprising:

a flask base and a flask bonnet, wherein the flask base comprises a bottom wall, side walls and a first flask neck part connected to a front side wall, the flask bonnet comprises a cover wall and a second flask neck part connected to the cover wall, the flask base and flask bonnet having adjacent margins, and the flask base and flask bonnet are connected to each other in a sealing manner at the adjacent margins;

a culture chamber in a flask body having an even bottom wall with a growth surface on a top side, an even cover wall at a section from the bottom wall, and the side walls that bridge the distance between the bottom wall and the even cover wall, the bottom wall and a top wall having a rectangular and a trapezoidal portion whereby the culture flask by the trapezoidal portion narrows towards the front side wall, an opening of the flask, the opening being formed into adjacent regions of the front side wall and the cover wall and in a center of the front side wall, the opening having a lower section provided in the front side wall and an upper section provided in the cover wall, the upper section having a form of a section of an ellipse in a plan view, a first hollow cylindrical neck part connected to a margin of the lower section, a second neck part being a hollow cylindrical segment formed by the cover wall and connected at lateral margins to an elliptical margin of the upper section, the elliptical margin having an end face margin, the end face margin being connected to a top margin section of a first neck part that projects upwards beyond the front side wall and the cover wall, respectively and the first and second neck parts form a hollow cylindrical flask neck that is aligned at a sharp angle to the growth surface, so that a pipette, a scraper, a cannula or another elongated device for adding or removing material can be placed on rear corners of the growth surface from the outside through the flask neck.

2. The culture flask according to claim 1, wherein the connection between the flask base and flask bonnet is an ultrasonic welded connection, or an infrared welded connection, or an adhesive connection, or a snap connection.

* * * * *